United States Patent
Zhang et al.

(10) Patent No.: US 12,292,433 B2
(45) Date of Patent: May 6, 2025

(54) ERT/ECT DUAL-MODALITY COMBINED THREE-DIMENSIONAL SENSOR

(71) Applicant: Qingdao University of Technology, Qingdao (CN)

(72) Inventors: Peng Zhang, Qingdao (CN); Wentao Wang, Qingdao (CN); Jiuwen Bao, Qingdao (CN); Shanbin Xue, Qingdao (CN)

(73) Assignee: Qingdao University of Technology, Qingdao (CN)

( * ) Notice: Subject to any disclaimer, the term of this patent is extended or adjusted under 35 U.S.C. 154(b) by 0 days.

(21) Appl. No.: 18/030,285

(22) PCT Filed: Jun. 16, 2022

(86) PCT No.: PCT/CN2022/099046
§ 371 (c)(1),
(2) Date: Apr. 5, 2023

(87) PCT Pub. No.: WO2023/093001
PCT Pub. Date: Jun. 1, 2023

(65) Prior Publication Data
US 2024/0369529 A1    Nov. 7, 2024

(30) Foreign Application Priority Data
Nov. 29, 2021   (CN) ........................ 202111433254.9

(51) Int. Cl.
*G01N 33/38*    (2006.01)
*G01N 27/04*    (2006.01)
(Continued)

(52) U.S. Cl.
CPC ......... *G01N 33/383* (2013.01); *G01N 27/041* (2013.01); *G01N 27/048* (2013.01); *G01N 27/223* (2013.01)

(58) Field of Classification Search
CPC ...... G01N 33/383; G01N 27/00; G01N 27/02; G01N 27/04; G01N 27/041; G01N 27/045; G01N 27/048; G01N 27/223
See application file for complete search history.

(56) References Cited

U.S. PATENT DOCUMENTS 10,378,941 B2 *   8/2019   McCann ................... G01F 1/60

FOREIGN PATENT DOCUMENTS

| CN | 1793879 | * | 6/2006 | ............. G01N 27/00 |
| CN | 101025404 | * | 8/2007 | ............. G01R 27/00 |

(Continued)

*Primary Examiner* — Neel D Shah
(74) *Attorney, Agent, or Firm* — Occhiuti & Rohlicek LLP (57) ABSTRACT

The present disclosure relates to an ERT/ECT dual-modality combined three-dimensional sensor. A cover box is sheathed with a shielding box, a plurality of small round holes are formed in the top surface and the side surfaces of the cover box, ERT electrodes are arranged in the small round holes, and ECT electrodes are arranged at the outer sides of the ERT electrodes. The ERT electrodes are connected to an ERT data acquisition box via electrode leads, and the ECT electrodes are connected to an ECT data acquisition box via the electrode leads. An integrated cuboid design in line with the concrete structure is employed. Meanwhile, the dimensions, combination modes, placement modes and positions, supporting structures, shielding devices, electrode leads and leading-out modes of two sets of electrode arrays are subjected to comprehensive optimization design to achieve three-dimensional visual nondestructive monitoring of the moisture intrusion process in the concrete structure.

16 Claims, 5 Drawing Sheets

(51) Int. Cl.
*G01N 27/22* (2006.01)
*G01R 27/02* (2006.01)

(56) References Cited

FOREIGN PATENT DOCUMENTS

| | | | | |
|---|---|---|---|---|
| CN | 112326744 | * | 10/2020 | ............ G01N 27/22 |
| WO | WO-2015142610 A1 | * | 9/2015 | ......... G01R 33/0041 |

\* cited by examiner

ERT/ECT DUAL-MODALITY COMBINED THREE-DIMENSIONAL SENSOR

CROSS-REFERENCE TO RELATED APPLICATION

This patent application is a 371 national stage application of International Application No. PCT/CN2022/099046, filed Jun. 16, 2022, which claims the benefit of the filing data of Chinese Patent Application No. 202111433254.9 filed with the China National Intellectual Property Administration on Nov. 29, 2021, entitled "ERT/ECT dual-modality combined three-dimensional sensor", the disclosures of which are entirely incorporated by reference herein.

TECHNICAL FIELD

The present disclosure belongs to the technical field of durability monitoring of concrete, and relates to an ERT/ECT dual-modality combined three-dimensional sensor capable of achieving three-dimensional visual nondestructive monitoring of moisture transport inside a concrete structure.

BACKGROUND

Concrete structures have become one of most widely used structural forms in the world, including house buildings, roads and bridges, special engineering, port and wharf engineering. However, concrete structures are inevitably affected by the external environment in the actual service process, resulting in different degrees of damage, making the durability gradually reduced. The durability of concrete structures has an important impact on the sustainable coordinated development of society and economy. Therefore, it is of a great significance to research the durability deterioration mechanism of concrete structure in depth and then take corresponding measures to improve its service life.

The durability damage of concrete structures involves a variety of deterioration reactions, with complicated influencing factors and deterioration mechanisms, but in the final analysis, the durability damage is related to the intrusion rate of moisture and harmful media carried by the moisture into the cement-based material. Therefore, detecting and quantifying the moisture intrusion process inside the cement-based material based on the visualization technology are the key to research the durability issue of the concrete structures. In the prior art, methods for visual monitoring and quantifying moisture transport include a nuclear magnetic resonance method, a ray attenuation method and an electrical monitoring method. The nuclear magnetic resonance method and the ray attenuation method both have high spatial resolution, but the equipment used is complicated and expensive, and the process of test measurement and quantitative analysis and calculation are extremely tedious. In contrast, the electrical monitoring method has the advantages of non-invasive, fast response, wide range of adaptation, low cost, no radiation, portability, etc. The electrical monitoring method is a multidisciplinary crossover of high technology, and has a wide application prospect in the visual monitoring of moisture transport inside the cement-based material.

The electrical monitoring method mainly includes an electrical resistance tomography (ERT) technology and an electrical capacitance tomography (ECT) technology which have the following commonalities in composition and function: 1) system construction: the ERT and the ECT both are composed of a sensor with electrode array, a data acquisition box and an imaging computer; (2) imaging principle: the ERT and the ECT are both based on the electromagnetic field theory, and the images of the changes of the moisture distribution inside the concrete over time is reconstructed by acquiring the changes of electrical signals in the measurement field by the sensors in real-time. Meanwhile, the ERT and the ECT have different characteristics and application ranges: the ERT is configured to measure the resistivity inside an object, the measurement field is equivalent to a resistance model, and electrodes are usually installed on the inner wall of the sensor to facilitate the injection of excitation current; while the ECT is configured to measure the dielectric constant inside the object, the measurement field is equivalent to a capacitance model, and electrodes are usually installed on the outer wall of the sensor. In addition, the ERT measurement requires good ohmic contact between the electrodes and the concrete structure, and is more suitable for detecting specimens with higher moisture content. In contrast, due to the fact that the dielectric constant contrast of the concrete to water is very high, the ECT measurement is extremely sensitive to the moisture in the concrete, and has a better effect for imaging the concrete structure with low moisture content. Based on the commonality and complementarity of the ERT and ECT, the ERT and ECT are combined to form an ERT/ECT dual-modality monitoring system, which is conducive to further improving the imaging accuracy of moisture distribution inside the concrete structure, widening the measurement range of a single technology, and effectively solving the problem that the imaging result of the single technology is lack of a comparison verification method.

Due to the inherent "soft field" characteristics of measurement fields of the ERT sensor and the ECT sensor, the sensitive field distribution is extremely non-uniform even without the sensors, affecting the accuracy of the reconstructed image, while the non-uniformity is closely related to the structural parameters of the sensors. Therefore, how to design the ERT/ECT dual-modality sensor with electrode array to reduce the influence of the nonlinear characteristics of the sensitive field and prevent the interaction effect between the two types of electrode arrays is the core and key technology to achieve the dual-modality imaging system and is an important prerequisite for imaging unsaturated moisture transport inside the concrete structure. At present. ERT/ECT dual-modality combined two-dimensional sensors have made preliminary research results in the field of multiphase flow monitoring. For example, an ERT/ECT dual-modality imaging system combined sensor array is disclosed in Chinese patent No. 200510122587.4, including the same number of ECT electrodes and ERT electrodes. The electrodes in the ERT electrode array and the ECT electrode array are respectively installed on the inner and outer walls of the same cross section of a measured fluid pipeline in a circumferentially uniform manner by the sealing of insulating washers and the fixing of nuts. The number of electrodes in the ERT electrode array and the ECT electrode array is 8 to 64, a radial shielding electrode is provided between every two ECT electrodes, and a shielding cover is arranged at the outermost of the ECT electrodes. The ERT electrodes in the combined electrode array are bolt-shaped and made of stainless steel, titanium alloy or silver chloride. The ECT electrodes in the combined electrode array are rectangular with holes in the middle and are made of metallic copper. By installing two sets of electrodes at the same cross section of the fluid pipeline, the flow field distribution information of the measured fluid is obtained, thus achieving the complementarity of ERT and ECT technologies. In Chinese Patent No. 200710056857.5, the improvement is made on the basis of Chinese patent No. 200510122587.4, and an ECT/ERT dual-modality imaging system crossed combined sensor array is provided, including the same number of ECT electrode array and ERT electrode array, which are uniformly and crosswise installed on the inner and outer walls of the cross section of a measured pipeline. The number of electrodes in the ECT electrode array and ERT electrode array is 8 to 64, and an ERT electrode is installed between every two ECT electrodes. A shielding cover is arranged outside the ERT electrodes, and the shielding cover is not in conduction with the electrodes. When the ECT electrode array operates, the ERT electrodes are in conduction with the ground via an analog electronic switch, thus becoming radial shielding electrodes of the ECT electrode array. Such design may reduce the dynamic range of the measured capacitance, and is beneficial to the measurement of the ECT system. However, the sensors mentioned in the above patent are only suitable for multiphase flow monitoring in the pipeline, and the papers and patent reports related to the ERT/ECT dual-modality combined sensor have not been published in the field of cement-based materials. Meanwhile, the existing sensors can only achieve two-dimensional detection of the fluid distribution in the pipeline, the acquisition is only an axial average result in the measurement field of the sensor, and there is no correlation between a plurality of two-dimensional images, so the dynamic running process of the fluid in the pipeline cannot be presented, and it is impossible to achieve a real sense of "visualization".

Therefore, based on the superiority and complementarity of the ERT and ECT in the moisture monitoring inside the cement-based materials, an ERT/ECT dual-modality combined three-dimensional sensor is provided by introducing the electrical monitoring technology by interdisciplinary, which provides a new idea and scientific means for further exploring the durability deterioration mechanism of the concrete structure, and has high social value and economic benefits.

SUMMARY

An objective of the present disclosure is to overcome the shortcomings of complex construction, small dynamic monitoring range, inadaptability to monitor concrete structures, inability to provide a three-dimensional detection result and lack of comparative verification methods in imaging results in the prior art, and to seek to design an ERT/ECT dual-modality combined three-dimensional sensor which is simple in construction, low in manufacturing cost, wide in dynamic monitoring range and integrated in structure and is capable of tracking the moisture intrusion process inside the concrete structure and providing technical and theoretical supports for the research on the durability issue of the concrete structure.

The present disclosure provides an ERT/ECT dual-modality combined three-dimensional sensor configured to be sheathed outside a concrete specimen. A main structure of the sensor comprises a cover box, a shielding box. ERT electrodes, ECT electrodes, and electrode leads. The shielding box is sheathed outside the cover box, a plurality of small round holes are formed in a top surface and side surfaces of the cover box, the ERT electrodes are arranged in the small round holes, and the ECT electrodes are arranged on outer sides of the ERT electrodes. The ERT electrodes are connected to an ERT data acquisition box via the electrode leads, and the ECT electrodes are connected to an ECT data acquisition box via the electrode leads.

In accordance with the present disclosure, a plurality of partition plates are arranged on the side surfaces of the cover box with a bottomless cuboid structure. A same large round hole is formed at a same eccentric position of each of top surfaces of the cover box and the shielding box, and a plurality of through holes are formed in the partition plates at an equal interval. A water injection pipe with scale marks is arranged at the large round hole of the shielding box, and the water injection pipe is fixedly arranged at an edge of the large round hole of the shielding box by a fixing seat. The ERT electrodes each are provided with a screw stem which is fastened via a nut; the ECT electrodes are arranged on portions of the cover box excluding the small round holes and are concentric with the ERT electrodes, and gaskets are provided between the nut and the ECT electrodes. The connection between the ERT electrodes and the ERT data acquisition box is achieved via the welding of the screw stem and the electrode leads, and the connection between the ECT electrodes and the ECT data acquisition box is achieved via the direct welding of the ECT electrodes and the electrode leads. The electrode leads penetrate out from the through holes.

In accordance with the present disclosure, the cover box employs an integrated design solution of five surfaces wrapped, thus the ERT electrodes and the ECT electrodes can be fixed better and extra errors caused by movement of the ERT electrodes and the ECT electrodes or replacement of a concrete specimen during testing can be avoided. The partition plates are configured to protect the ERT electrodes and the ECT electrodes from being abraded and damaged while fixing the position of the shielding box. The shielding box is a metal shielding housing employing an integrated design solution of five surfaces sealed, which can reinforce the overall structure on the premise of effectively preventing external electromagnetic field interference. The through holes are favorable for leading the electrode leads out, and the through holes are in one-to-one correspondence with the electrode leads to avoid the winding and abrasion and signal influence between the electrode leads. The fixing seat can increase the contact area between the fixing seat and the concrete member, thereby preventing moisture leakage and deviation of the water injection pipe during testing. The eccentric design of the water injection pipe is beneficial to inducing non-uniform three-dimensional moisture penetration, making the moisture penetration in line with the moisture diffusion inside the concrete specimen in the actual service process; the scale marks on the surface of the water injection pipe is more convenient for real-time observation of the content of moisture intruding into the concrete specimen, and thus time-based visual quantitative imaging of a moisture distribution inside the concrete specimen is achieved. The ERT electrodes are of round steel sheet structure having better wear resistance and corrosion resistance, and are arranged on the surface of the concrete specimen in an array to facilitate the electrical current injection, without affecting measurement results of the ECT electrodes. The ECT electrodes are of square copper sheet structure and are arranged on the outer walls of the cover box in an array to effectively increase the coverage range and enhance the signal strength; and the ECT electrodes can be better protected from being damaged via the external arrangement mode. The gasket is made of rubber and thus can prevent the ECT electrodes from being twisted and deformed due to compression.

In accordance with the present disclosure, the bottom of the cover box and the bottom of the shielding box each are opened to facilitate the nesting and take-out of the concrete specimen, and the ERT electrodes and the ECT electrodes do not need to be detached in this process, thus the errors caused by displacement of the ERT electrodes and the ECT electrodes are avoided. Five surfaces of the concrete specimen are covered with the ERT electrodes and the ECT electrodes, increasing the number of detected signals which is conducive to accurately detecting the whole process of moisture intrusion and improving the imaging precision and the detection range. Due to the design solution that the ERT electrodes are placed in holes reserved in the middles of the ECT electrodes, the ERT electrodes do not need to occupy more space, and the overall structure is simplified. Moreover, mutual interference between two sets of electrode arrays can be avoided due to the solution that the two sets of electrode arrays are placed in an inner-outer separated manner. Meanwhile, the two sets of electrode arrays are uniformly distributed on the five surfaces of the cover box to facilitate the acquisition of moisture dynamic signals at the same time and at the same position, thus achieving the complementarity and comparison of the ERT measurement and ECT measurement.

Compared with the prior art, by improving a conventional sensor via interdisciplinary and applying the sensor to the field of durability monitoring of the concrete structure, a conventional cylinder design solution is abandoned, and an integrated cuboid design in line with the concrete structure is employed. Meanwhile, the dimensions, combination modes, placement modes and positions, supporting structures, shielding devices, electrode leads and leading-out modes of the two sets of electrode arrays are subjected to comprehensive optimization design to achieve three-dimensional visual nondestructive monitoring of the moisture intrusion process inside the concrete structure, thus providing a scientific means for durability research of the concrete structure. The device is firm in structure, high in durability, low in manufacturing cost, small in occupied space and wide in detection range, and capable of achieving interactive, multi-dimensional and visual quantitative detection of the moisture intrusion process inside the concrete structure, therefore the problem of dynamic three-dimensional imaging comparative analysis of moisture transport of the same material at the same time and at the same position is effectively solved, and the defects of the conventional sensor in space imaging are overcome.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts shall fall within the scope of the present disclosure.

An objective of the present disclosure is to overcome the shortcomings of complex construction, small dynamic monitoring range, inadaptability to monitor concrete structures, inability to provide a three-dimensional detection result and lack of comparative verification methods in imaging results in the prior art, and to provide an ERT/ECT dual-modality combined three-dimensional sensor which is simple in construction, low in manufacturing cost, wide in dynamic monitoring range and integrated in structure and is capable of tracking the moisture intrusion process inside the concrete structure and providing technical and theoretical supports for the research on the durability issue of the concrete structure.

To make the objective, features and advantages above of the present disclosure more apparent and understandable, the present disclosure is further described in detail below with reference to the accompanying drawings and specific embodiments.

Embodiment I

Figure 1:
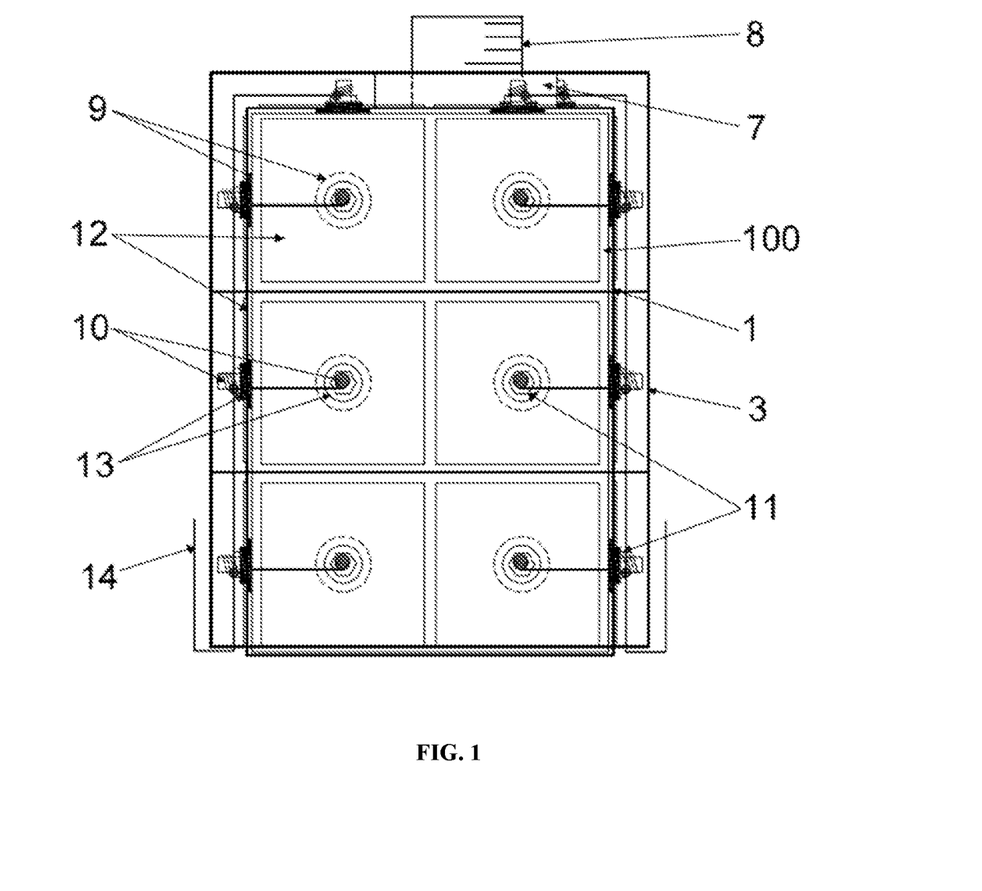
FIG. 1 is a front view of a main structure of the present disclosure.
Figure 2:
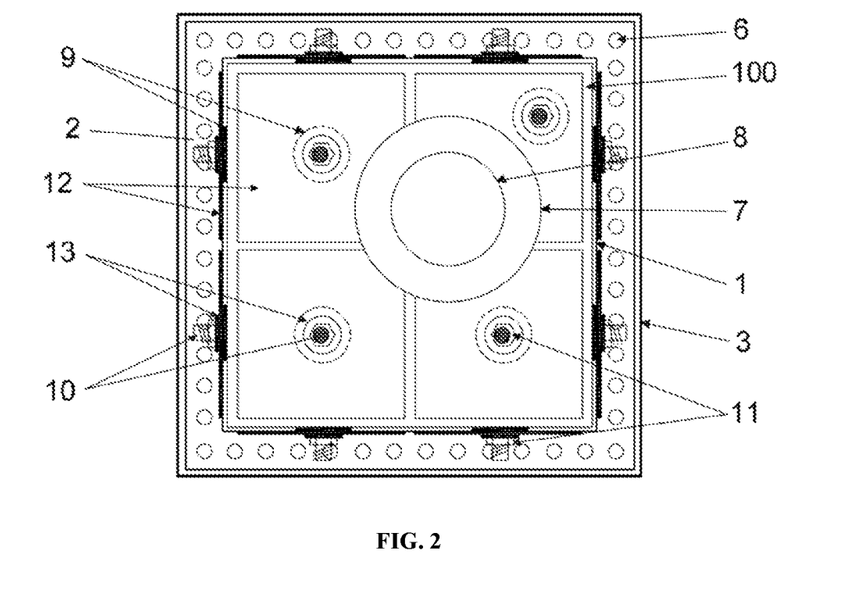
FIG. 2 is a top view of a main structure of the present disclosure.
Figure 3:
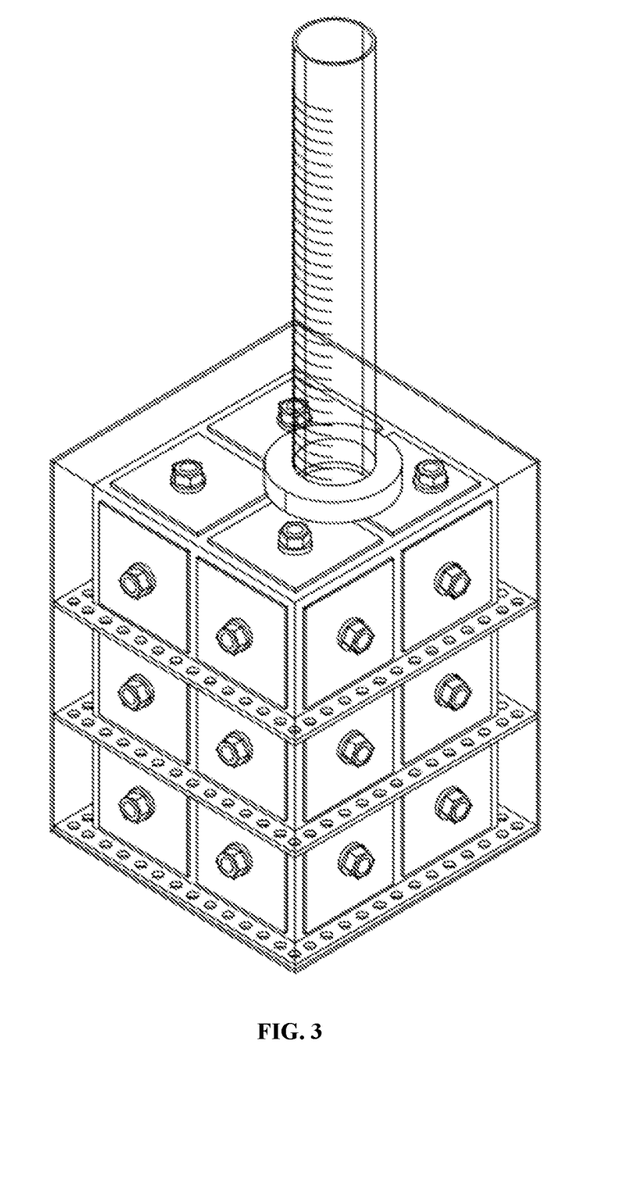
FIG. 3 is a schematic diagram of a three-dimensional structure of the present disclosure.
Figure 4:
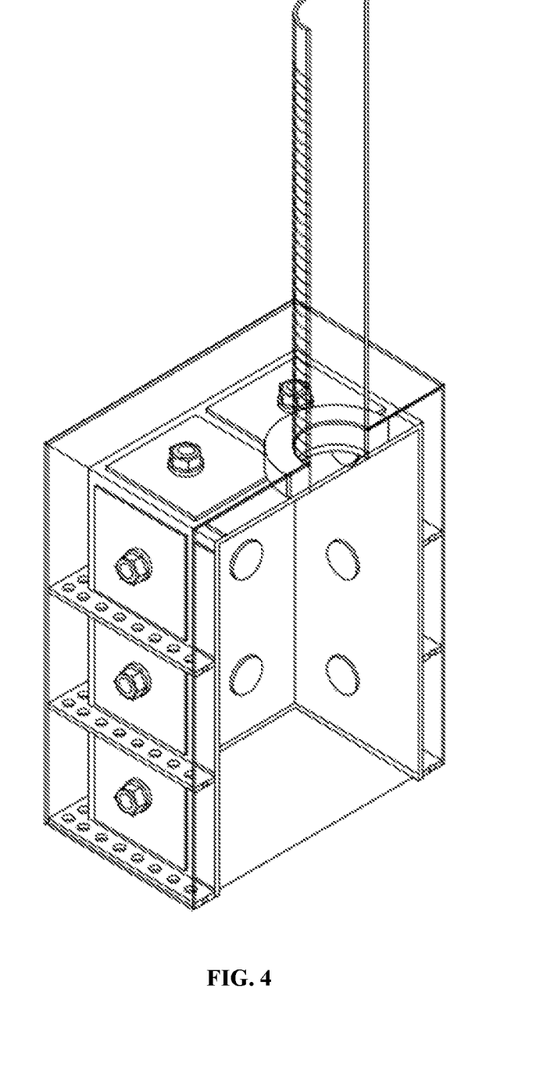
FIG. 4 is a schematic cross-sectional view of a three-dimensional structure of the present disclosure.
Figure 5:
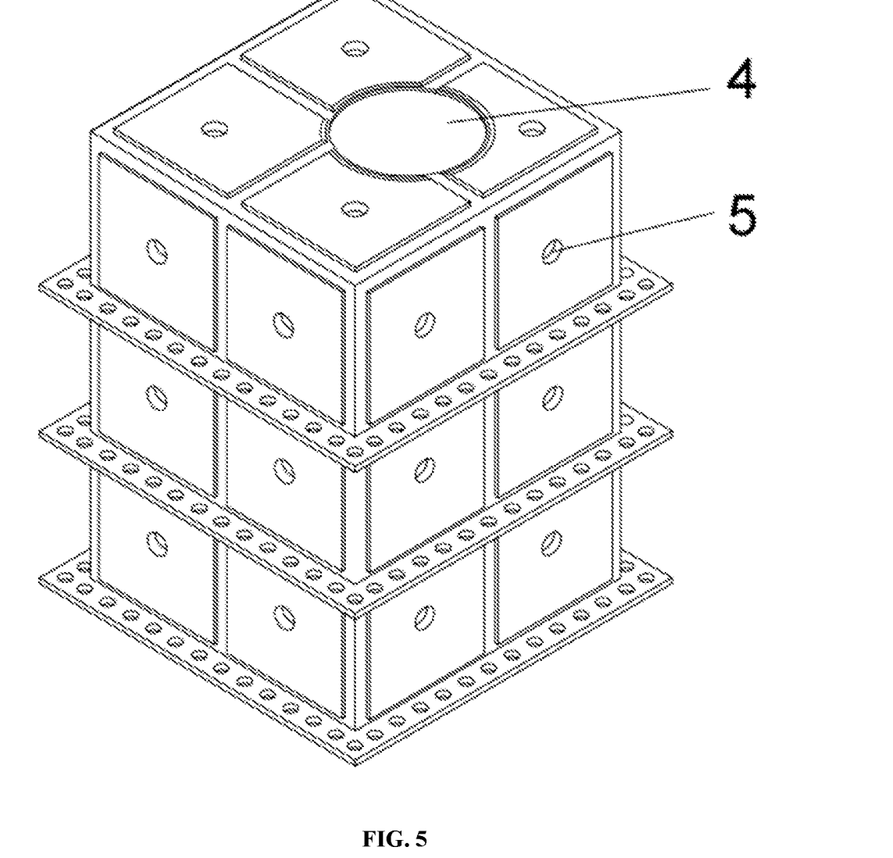
FIG. 5 is a schematic diagram of a three-dimensional structure of a cover box in accordance with the present disclosure.

An ERT/ECT dual-modality combined three-dimensional sensor in accordance with the embodiment may achieve the visual tracking of moisture intrusion process inside a concrete structure. A main structure of the sensor comprises a cover box 1, partition plates 2, a shielding box 3, large round holes 4, small round holes 5, through holes 6, a fixing seat 7, a water injection pipe 8, ERT electrodes 9, screw stems 10, nuts 11, ECT electrodes 12, gaskets 13, and electrode leads 14. Three partition plates 2 are arranged on the side surface of the cover box 1 with a bottomless cuboid structure at an equal interval, the shielding box 3 without bottom is sheathed outside the cover box 1, and the same large round hole 4 is formed at the same eccentric position of each of the top surfaces of the cover box 1 and the shielding box 3, twenty-eight small round holes 5 are formed in the top surface and the side surfaces of the cover box 1, and fifty-two through holes 6 are formed in each of the partition plates 2 at an equal interval. The fixing seat 7 with a circular structure is arranged at the edge of the large round hole 4 of the shielding box 3, and the water injection pipe 8 with scale marks is arranged in the fixing seat 7. The ERT electrodes 9 are arranged in the small round holes 5 and are provided with the screw stems 10, and the screw stems 10 are fastened via the nuts 11. The ECT electrodes 12 concentric with the ERT electrodes 9 are arranged on portions of the cover box 1 excluding the small round holes 5, and the gaskets 13 are arranged between the nuts 11 and the ECT electrodes 12. The ERT electrodes 9 are connected to an ERT data acquisition box via the welding of the screw stems 10 and the electrode leads 14, the ECT electrodes 12 are connected to an ECT data acquisition box via the direct welding of the electrodes 12 and the electrode leads 14, and the electrode leads 14 penetrate out from the through holes 6.

In accordance with the embodiment, the cover box 1 is of an integrated insulating structure which is prepared by the 3D printing technology and has a thickness of 2 mm. The partition plates 2 each have an extending width of 1 cm; the shielding box 3 has a length of 12.4 cm, a width of 12.4 cm, a height of 16.2 cm, and a thickness of 1 mm. The large round holes 4 each have a diameter of 5 cm to facilitate the placement of the fixing seat 7. The small round holes 5 each have a diameter of 5 mm. The through holes 6 each have a diameter of 0.5 mm. The fixing seat 7 is an acrylic circular ring having an outer diameter of 5 cm, a height of 1 cm and a thickness of 1 cm, and is configured to increase the contact area of the water injection pipe 8 and the concrete specimen 100. The water injection pipe 8 is a bottomless acrylic cylinder having an outer diameter of 3 cm, a height of 20 cm and a thickness of 1 mm, and the scale marks printed on the surface of the water injection pipe 8 are convenient for the real-time observation of the water absorption of the concrete specimen 100. The fixing seat 7 and the water injection pipe 8 are pasted and arranged in a length direction and a width direction of the top surface of the concrete specimen 100 at an offset of 1 cm, respectively, thus inducing non-uniform moisture penetration. The ERT electrodes 9 each are circular steel sheets having a diameter of 1.5 cm and a thickness of 0.1 mm. The ECT electrodes 12 each are cuboid copper sheets having a side length of 4.5 cm and a thickness of 0.1 mm. The ERT electrodes 9 and the ECT electrode 12 are uniformly pasted to the five surfaces of the cover box 1 The ECT electrodes 12 at the top surface of the cover box 1 are cut along the edge of the fixing seat 7, where one of the ERT electrodes 9 at the top surface of the cover box 1 is outwards deviated by 1 cm along with the fixing seat 7, other ERT electrodes 9 are located on the centers of the ECT electrodes 12. The screw stems 10 are welded to the outer sides of the ERT electrodes 9 via tin soldering, extends outward and are fixed by the nuts 11. The gaskets 13 each have a diameter of 1 cm and a thickness of 1 mm. The electrode leads 14 each are radio-frequency coaxial cables having a diameter of 3 mm, and are respectively connected to the screw stems 10 and the ECT electrodes 12 via tin soldering, and penetrate out from the through holes 6 to be connected to the data acquisition box.

Embodiment II

The main structure of an ERT/ECT dual-modality combined three-dimensional sensor in accordance with the embodiment is the same as the main structure in accordance with the embodiment I. The technical process for achieving visual tracking of the moisture intrusion and transport process inside a concrete structure includes the following steps:

Step one, preparing a cuboid-shaped concrete specimen 100 with a cuboid structure having a length of 10 cm, a width of 10 cm and a height of 15 cm according to a set mixing proportion; after being maintained in a standard maintaining room for 7 days, placing the concrete specimen 100 in a blast drying box to be dried to a constant weight; and then pasting a fixing seat 7 and a water injection pipe 8, which are pasted and combined into a whole, to the eccentric position of the top surface of the concrete specimen 100 cooled to the room temperature.

The pasting at the two positions both employs an oily glue pasting mode.

Step two, uniformly pasting ECT electrodes 12 to five surfaces of the cover box 1 and cutting and trepanning the cover box 1 at the positions corresponding to a large round hole 4 and small round holes 5 so as to form through holes; welding screw stems 10 to the center positions of the surfaces of the ERT electrodes 9, such that the screw stems 10 pass through the small round holes 5 and are fixed by rotating the nuts 11, and then welding electrode leads 14 to the surfaces of the screw stems 10 and the ECT electrodes 12, the electrode leads 14 pass through the through holes 6 and then penetrate out from the bottom of the cover box 1; sheathing the concrete member 100 form the bottom of the cover box 1, such that the five surfaces of the concrete member are tightly attached to the five surfaces of the cover box 1, and then sheathing the shielding box 3 from the top of the cover box 1 to complete the whole packaging and assembling of the sensor.

Step three, connecting the electrode leads 14 to an ERT data acquisition box and an ECT data acquisition box, respectively; and connecting the ERT data acquisition box and the ECT data acquisition box to an imaging computer via data transmission lines so as to form a complete monitoring system.

Firstly, turning on the ERT data acquisition box to acquire a resistance signal of the dry concrete specimen 100 as a reference value, and at the moment, the ECT data acquisition box is in a standby state; then turning on the ECT data acquisition box and pausing the ERT data acquisition box so as to acquire a capacitance signal as a reference value, thus eliminating the interaction effect between the ERT electrodes and the ECT electrodes; finally, adding deionized water into the water injection pipe 8, and acquiring the changes of the resistance/capacitance signals inside the concrete specimen 100 according to above steps while recording the moisture intrusion content regularly.

Step four, integrating the acquired resistance/capacitance signals and performing image reconstruction via an image reconstruction algorithm on the imaging computer, achieving the visual quantitative imaging of the moisture transport process of the same material at the same position and the same time; then comparing and analyzing the ERT reconstructed image and the ECT reconstructed image so as to solve the problem that a single imaging technology lacks a comparison verification method.

The various embodiments in the specification are described in a progressive manner, the differences from other embodiments are illustrated in each embodiment, and reference can be made to other embodiments for understanding the same or similar parts of the embodiments.

Several examples are used for illustration of the principles and implementation methods of the present disclosure. The description of the embodiments is merely used to help illustrate the method and its core principles of the present disclosure. In addition, those of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. An electrical resistance tomography (ERT)/electrical capacitance tomography (ECT) dual-modality combined three-dimensional sensor configured to be sheathed outside a concrete specimen; wherein the ERT/ECT dual-modality combined three dimensional sensor comprises a main structure comprising a cover box, a shielding box, ERT electrodes, ECT electrodes, and electrode leads; the shielding box is sheathed outside the cover box, a plurality of small round holes are formed in a top surface and side surfaces of the cover box, the ERT electrodes are arranged in the small round holes, and the ECT electrodes are arranged on outer sides of the ERT electrodes; and the ERT electrodes are connected to an ERT data acquisition box via the electrode leads, and the ECT electrodes are connected to an ECT data acquisition box via the electrode leads, wherein a plurality of partition plates are arranged on the side surfaces of the cover box; a same large round hole is formed at a same eccentric position of each of top surfaces of the cover box and the shielding box, and a plurality of through holes are formed in the partition plates an equal interval; a water injection pipe with scale marks is arranged at the large round hole of the shielding box, and the water injection pipe is fixedly arranged at an edge of the large round hole of the shielding box by a fixing seat; the ERT electrodes each are provided with a screw stem which is fastened via a nut; the ECT electrodes are arranged on portions of the cover box excluding the small round holes and are concentric with the ERT electrodes, and gaskets are provided between the nut and the ECT electrodes; connection between the ERT electrodes and the ERT data acquisition box is achieved by welding of the screw stem and the electrode leads, and connection between the ECT electrodes and the ECT data acquisition box is achieved by direct welding of the ECT electrodes and the electrode leads, and the electrode leads all penetrate out from the through holes.

2. The ERT/ECT dual-modality combined three-dimensional sensor according to claim 1, wherein the cover box and the shielding box each are sealed on five side surfaces and opened on a bottom surface; the ERT electrodes and the ECT electrodes do not need to be detached when the concrete specimen is nested in, or taken out of, the cover box, wherein the shielding box is a metal shielding housing.

3. The ERT/ECT dual-modality combined three-dimensional sensor according to claim 2, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

4. The ERT/ECT dual-modality combined three-dimensional sensor according to claim 1, wherein the partition plates are configured to protect the ERT electrodes and the ECT electrodes from being abraded and damaged while fixing a position of the shielding box.

5. The ERT/ECT dual-modality combined three-dimensional sensor according to claim 4, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

6. The ERT/ECT dual-modality combined three-dimensional sensor according to claim 1, wherein the through holes are in one-to-one correspondence with the electrode leads to avoid winding, abrasion and signal influence between the electrode leads.

7. The ERT/ECT dual-modality combined three-dimensional sensor according to claim 6, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

8. The ERT/ECT dual-modality combined three-dimensional sensor according to claim 1, wherein the fixing seat is able to increase a contact area between the water injection pipe and the concrete specimen, thereby preventing moisture leakage and deviation of the water injection pipe during testing.

9. The ERT/ECT dual-modality combined three-dimensional sensor according to claim 8, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

10. The ERT/ECT dual-modality combined three-dimensional sensor according to claim 1, wherein eccentric design of the water injection pipe is beneficial to inducing non-uniform three-dimensional moisture penetration, making the moisture penetration in line with moisture diffusion inside the concrete specimen in actual service process; the scale marks on a surface of the water injection pipe is more convenient for real-time observation of content of moisture intruding into the concrete specimen, and thus time-based visual quantitative imaging of a moisture distribution inside the concrete specimen is achieved.

11. The ERT/ECT dual-modality combined three-dimensional sensor according to claim 10, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

12. The ERT/ECT dual-modality combined three-dimensional sensor according to claim 1, wherein the ERT electrodes are of round steel sheet structure and are arranged on a surface of the concrete specimen in an array to facilitate electrical current injection; the ECT electrodes are of square copper sheet structure and are arranged on outer walls of the cover box in an array; five surfaces of the concrete specimen are covered with the ERT electrodes and the ECT electrodes, thus facilitating acquisition of moisture dynamic signals at a same time and at a same position, achieving complementarity and comparison of ERT measurement and ECT measurement and increasing number of detected signals, which is conducive to accurately detecting whole process of moisture intrusion and improving imaging precision and detection range; and due to a fact that the ERT electrodes are placed in holes reserved in middles of the ECT electrodes, the ERT electrodes do not need to occupy more space, and mutual interference is avoided.

13. The ERT/ECT dual-modality combined three-dimensional sensor according to claim 12, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

14. The ERT/ECT dual-modality combined three-dimensional sensor according to claim 1, wherein the gaskets are made of rubber and thus are able to prevent the ECT electrodes from being twisted and deformed due to compression.

15. The ERT/ECT dual-modality combined three-dimensional sensor according to claim 14, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

16. The ERT/ECT dual-modality combined three-dimensional sensor according to claim 1, wherein a process for achieving visual tracking of moisture intrusion and moisture transport inside a concrete structure comprises following steps:

step one, preparing a cuboid-shaped concrete specimen having a set dimension according to a set mixing proportion; placing the concrete specimen, after being maintained in a standard maintaining room, in a blast drying box, and drying the concrete specimen to a constant weight; pasting the fixing seat and the water injection pipe, which are pasted and combined into a whole, to an eccentric position of a top surface of the concrete specimen cooled to a room temperature;

step two, uniformly pasting ECT electrodes to five surfaces of the cover box, and cutting and trepanning the cover box at positions corresponding to the large round hole and the small round holes to form through holes; welding the screw stems to center positions of surfaces of the ERT electrodes, enabling the screw stems to pass through the small round holes and to be fixed by rotating the nuts, and then welding the electrode leads to surfaces of the screw stems and the ECT electrodes, enabling the electrode leads to pass through the through holes and then to penetrate out from a bottom of the cover box; sheathing the concrete specimen from the bottom of the cover box, and then sheathing a shielding box from a top of the cover box, thus completing whole packaging and assembling of the sensor;

step three, connecting the electrode leads to an ERT data acquisition box and an ECT data acquisition box, respectively; and connecting the ERT data acquisition box and the ECT data acquisition box to an imaging computer via data transmission lines, thus forming a complete monitoring system:

firstly, turning on the ERT data acquisition box to acquire a resistance signal of the dry concrete specimen as a reference value, the ECT data acquisition box being in a standby state at the moment; then turning on the ECT data acquisition box and pausing the ERT data acquisition box so as to acquire a capacitance signal as a reference value, thus eliminating interaction effect between the ERT electrodes and the ECT electrodes; finally, adding deionized water into the water injection pipe, and acquiring changes of resistance/capacitance signals inside the concrete specimen according to above steps while recording moisture intrusion content regularly; and step four, integrating the acquired resistance/capacitance signals, performing image reconstruction by an image reconstruction algorithm on the imaging computer, thus achieving visual quantitative imaging of moisture transport process of a same material at a same position and a same time; and comparing and analyzing ERT and ECT reconstructed images.

\* \* \* \* \*